United States Patent [19]
Watts et al.

[11] Patent Number: 5,840,341
[45] Date of Patent: Nov. 24, 1998

[54] DRUG DELIVERY COMPOSITION CONTAINING CHITOSAN OR DERIVATIVE THEREOF HAVING A DEFINED Z. POTENTIAL

[75] Inventors: Peter James Watts; Lisbeth Illum, both of Nottingham, United Kingdom

[73] Assignee: Danbiosyst UK Limited, Nottingham, United Kingdom

[21] Appl. No.: 809,158

[22] PCT Filed: Aug. 21, 1995

[86] PCT No.: PCT/GB95/01980

§ 371 Date: Apr. 21, 1997

§ 102(e) Date: Apr. 21, 1997

[87] PCT Pub. No.: WO96/05810

PCT Pub. Date: Feb. 29, 1996

[30] Foreign Application Priority Data

Aug. 20, 1994 [GB] United Kingdom .................... 9416884

[51] Int. Cl.$^6$ .............. A61K 9/50; B01J 13/02; B32B 5/16; A01N 25/12

[52] U.S. Cl. .................. 424/499; 514/777; 264/4.1; 428/402

[58] Field of Search ................... 424/499, 500; 514/777; 264/4.1; 428/402

[56] References Cited

U.S. PATENT DOCUMENTS 5,129,877 7/1992 Gallo et al. ......................... 600/12

FOREIGN PATENT DOCUMENTS

WO 90/09780 9/1990 WIPO .
WO 93/15737 8/1993 WIPO .

*Primary Examiner*—Carlos Azpuru
*Attorney, Agent, or Firm*—Arnall, Golden & Gregory, LLP

[57] ABSTRACT

A drug delivery composition for administration to mucosa is provided. The composition includes a pharmacologically active compound and particles, preferably powder or microspheres, of chitosan or a chitosan derivative or salt wherein the particles are either solidified or partially cross-linked such that they have a zeta potential of +0.5 to +50 mV. Solidified particles are made by treating particles made from a water soluble chitosan salt with an alkaline agent such as sodium hydroxide in a non-acid containing water to render them insoluble.

13 Claims, 9 Drawing Sheets

DRUG DELIVERY COMPOSITION CONTAINING CHITOSAN OR DERIVATIVE THEREOF HAVING A DEFINED Z. POTENTIAL

RELATED APPLICATIONS

Priority is claimed under 35 U.S.C. §119 to PCT/GB95/01980, filed Aug. 21, 1995, which corresponds to GB 9416884.6, filed Aug. 20, 1994.

The present invention relates to drug delivery compositions and more particularly to compositions based on chitosan microparticles which provide for the improved uptake of active drug material across mucosal surfaces, such as the vagina, the small intestine, the colon, the lungs, the rectum, the eye, the buccal cavity or the nasal cavity.

BACKGROUND OF THE INVENTION

A major problem in drug delivery is the effective absorption of polar molecules, that include high molecular weight material such as proteins and peptides, across biological membranes. Normally such molecules are not well taken up by the body if administered to the gastrointestinal tract, the buccal mucosa, the rectal mucosa, the vaginal mucosa or the intranasal mucosa. By a polar molecule, we mean a substance that has an octanol/water partition coefficient of less than 50. Recent studies with insulin have demonstrated that the absorption of such a compound can be increased if it is given together with a so-called absorption enhancer. These absorption enhancing materials have included surfactants of the non-ionic type as well as various bile salt derivatives. An increased permeability of membranes in the presence of these types of surfactant materials is obtained and the literature in the field of pharmaceutical sciences contains a wide range of such absorption promoters. (For a review see Davis et al (editors), *Delivery Systems for Peptide Drugs*, Plenum Press, New York, 1987). However, such materials are sometimes unacceptable because of their irritant effects on membranes. These include not only the non-ionic variety of surface active agents but also bile salts and bile salt derivatives (eg fusidic acid).

European Patents 023,359A and 122,023A describe a powdery pharmaceutical composition for application to the nasal mucosa and methods for administration thereof. The pharmaceutical composition allows polypeptides and derivatives thereof to be effectively absorbed through the nasal mucosa. Similarly, U.S. Pat. No. 4,226,849 describes a method for administering a powdery medicament to the nasal mucosa where the preferred composition has mucoadhesive properties.

Formulations based on microspheres for mucosal delivery have been described in WO 88/09163. The formulations contain certain enhancers to aid effective penetration of the mucosa by the drug. WO89/03207 further describes formulations which do not require an enhancer.

WO 90/09780 describes a composition consisting of a drug and a polycationic substance including chitosan that promotes the transport of the drug across mucosal membranes. The composition can also comprise microspheres of the polycationic substance.

Chitosan is deacetylated chitin, or poly-N-acetyl-D-glucosamine. It is available from Protan Laboratories, Inc. Redmond, Wash. 98052, U.S.A. and, depending on the grade selected, can be soluble in water up to pH 6.0. Chitosan has previously been used to precipitate proteinaceous material, to make surgical sutures and as an immunostimulant. It has also been employed previously in oral drug formulations in order to improve the dissolution of poorly soluble drugs (Sawayanagi et al, *Chem. Pharm. Bull.,* 31, 1983, 2062–2068) or for the sustained release of drugs by a process of slow erosion from a hydrated compressed matrix (Nagai et al *Proc. Jt. US Jpn. Semin. Adv. Chitin. Chitosan. Relat. Enzymes,* 21–39. Zikakis J. P. (ed), Academic Press. Orlando (1984)).

Chitosan microspheres have been produced for use for example for enhanced chromatographic separation (Li Q. et al, *Biomater. Artif. Cells Immobilization Biotechnol,* 21, 1993, 391–8) for topical delivery of drugs (Machida Y, Yakugaku Zasshi, 113, 1993, 356–68) for drug targeting after injection (Ohya Y et al, *J. Microencapsul.* 10, 1993, 1–9) and for controlled release of drugs (Bodmeier R. et al, *Pharm Res.* 6, 1989, 413–7, Chithambara et al *J. Pharm. Pharmacol.* 44, 1992, 283–286).

EP 454044 and EP486959 describe polyelectrolyte microparticles or polysaccharide microspheres including chitosan microspheres for controlled slow release of drugs. The drug is chemically bound or adsorbed to the surface.

Glutaraldehyde cross linked chitosan microspheres have been described in JP 539149 (Taisho Pharm. Co.). The use of chitosan as a biodegradable polymer material that is then modified by an amphiphilic polymer and an agent modifying the interface properties has been described in EP 486959 (Vectorpharma).

The standard method for the preparation of non-dissolving chitosan microspheres or microcapsules is to use an emulsification method. For example Chithambara et al (Cross-linked chitosan microspheres preparation and evaluation as a matrix for controlled release of pharmaceuticals, *J. Pharm. Pharmacol.* 44, 1992, 283–286) describe how an aqueous acetic acid dispersion of chitosan in paraffin oil using dioctylsulphosuccinate as a stabilising agent was cross-linked by glutaraldehyde. A similar emulsion cross-linking procedure was described by Hassan et al (Optimized formulation of magnetic chitosan microspheres containing the anticancer agent, oxantrazole, *Pharm. Research* 9, 1992, 390). Microspheres made from the complexation of chitosan with other polymers but of opposite charge have been described in papers and patents (EP 454044 to Hoechst AG).

Ionotropic gelation of chitosan by tripolyphosphate has been reported by Bodmeier et al (*Pharm. Research* 6, 1989, 413). The chitosan beads so prepared disintegrated at acid pH.

Microspheres intended to be bioadhesive have been described by Mathiowitz et al in PCT/US/03822. The microspheres were characterised by having a bioadhesive force of at least 11 $mN/cm^2$ as measured in a tensile test in the rat intestine. The attachment of positively charged ligands to microspheres to improve adhesion due to the electrostatic attraction of the cationic groups coating the beads, to the net negative charge of the mucus is mentioned as a possible strategy. The preparation of chitosan microspheres is described. The particles were prepared using a 1% chitosan concentration at pH 5.0. They were cross-linked using tripolyphosphate (3%). The particles so prepared were apparently of a size of approximately 2000 $\mu$m. It is noted that chitosan microparticles were found not to be satisfactory since the force of detachment per projected surface area ($mN/cm^2$) for such particles was less than 5 $mN/cm^2$.

SUMMARY OF THE INVENTION

It has now been found that positively charged solidified or partially cross-linked chitosan particles are able to considerably improve the absorption of drugs across mucosal tissue. They appear to do so by prolonging the known absorption promoting effect of the chitosan resulting in a sustained absorption. This is surprising since chitosan in solution gives rise to a pulsed absorption profile similar to the one obtained when using bioadhesive microspheres such as starch (WO 88/09163, WO 89/03207).

It is therefore an object of the present invention to provide drug delivery compositions for administration to mucosa, which include a pharmacologically active compound and particles of chitosan or a chitosan derivative or salt, wherein the particles are either solidified or partially cross-linked such that they have a zeta potential of +0.5 to +50 mV.

Preferably the particles are either microspheres or powder.

DETAILED DESCRIPTION OF THE INVENTION

Figure 1:
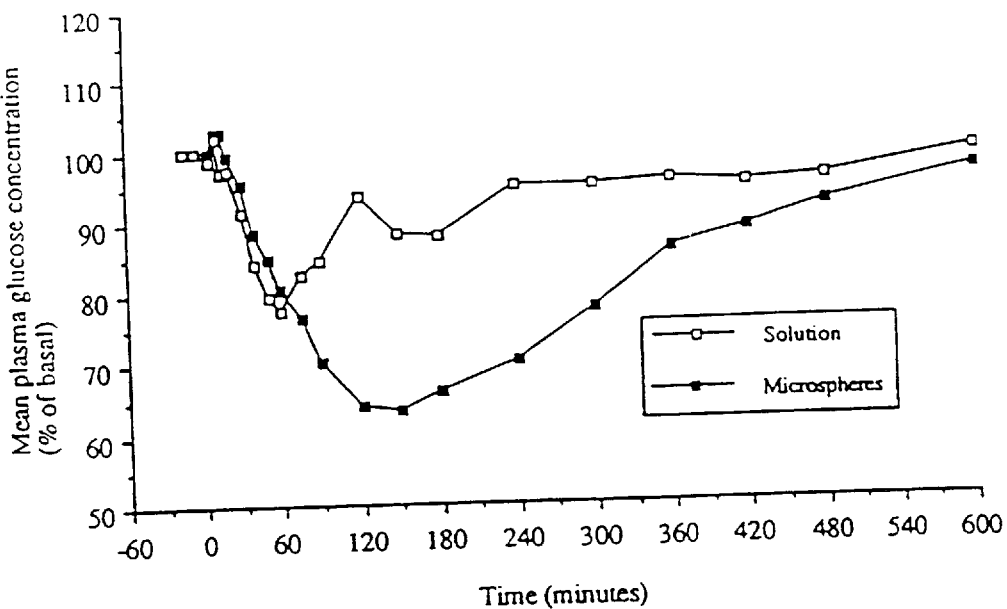
FIG. 1 is a graph showing the mean plasma glucose/time curves after administration to sheep of 2 IU/kg insulin in chitosan solution and with chitosan microspheres (prepared by emulsion heat method followed by formaldehyde treatment).

The surface charge of the particles expressed as the zeta potential is determined at pH 7.4 and 0.1M ionic strength. The method by which the zeta potential is measured depends on the size of the particles. For particles of 5 $\mu$m or more, the zeta potential is measured by microelectrophoresis using for example a Rank Mark II microelectrophoresis apparatus (Rank Bros., Cambridge). For particles below 5 $\mu$m, the zeta potential is measured by Laser Doppler Anemometry (LDA) using for example a Malvern Zeta Sizer IV (Malvern, UK).

Microelectrophoresis

For microelectrophoretic studies, a Rank Mark II microelectrophoresis apparatus (Rank Bros., Cambridge) can be used. A cylindrical glass microelectrophoresis cell is placed in a thermostated water bath at 25° C. Platinum black electrodes, prepared by oxidation in platinum chloride, are placed at either end of the cell. Illumination is by a 40 mW gas laser (Scientific and Cook Electronic, UK). The, movement of the particles is viewed by means of a binocular microscope system.

The interelectrode distance is calculated by measuring the conductivity of standard solutions of potassium chloride of for example 0.10M and 0.01M ionic strength at 25° C. The specific conductivity is the reciprocal of the resistance of a 1 m long and 1 m$^2$ in cross-section column of solution $$\text{(ie) } k = \frac{l}{\pi a^2 R}$$

where k is the conductivity, l the inter-electrode distance and R the resistance of the cell. The resistance is determined by measuring the change in current for a known change in voltage.

For the determination of the particle mobility the cell is filled with the appropriate buffer system (0.1M ionic strength, for example phosphate buffer or McIlvaine buffer, pH =7.4) and 1% w/v of the particles suspended in the buffer.

The suspension is left to equilibrate at 25° C. for 5 minutes before any measurements are taken. The electrodes are placed at each end of the cell to form a tight seal. A voltage in the range 20–60 volt is applied across the electrodes to give a reasonable transit time which reduces errors due to Brownian motion and operator timing. The velocity of individual particles is timed across a fixed distance, such as 30 $\mu$m calculated from an eyepiece graticule. Alternative measurements are taken with the electrode polarity reversed to prevent electrode polarization. The velocity of fifteen particles in each direction and at two voltages are measured and the electrophoretic mobility (u) calculated from $$u = \frac{V}{E}$$

where V is the particle velocity ($\mu$ms$^{-1}$). The electrophoretic mobilities can be converted to zeta potentials ($\xi$) using the equation derived by Smoluchowski (1903)

$$U = \frac{\epsilon \zeta}{4\pi\eta}$$

where $\epsilon$ is the permittivity and $\eta$ the viscosity of the dispersion medium. Assumptions are made as to the values of $\epsilon$ and $\eta$ in the electrical double layer. As a guideline the zeta potential can be obtained from the electrophoretic mobility by multiplying by approximately 15.

Laser Doppler Anemometry

Laser Doppler Anemometry involves the detection of scattered laser light from particles which are moving in an applied electric field. The equipment used can for example be a Malvern Zetasiser II (Malvern Instruments). The sample is illuminated with a laser light source (15 mW Helium-Neon laser) which is split into two beams of equal intensity. The split beams are then forced to cross to give an ellipsoid measuring volume; consisting of dark and light bands. The interference fringe pattern will be dependent on the beam crossing angle and the laser frequency. Particles moving under the application of an electric field will scatter light from the incident beam. The frequency shift–the Doppler frequency, Fd– is a function of the particle velocity as described by $$Fd = 2 \sin(\lambda\theta/2)u$$

where $\theta$ is the detection angle, $\lambda$ the laser wavelength and u the particle velocity, respectively. The Malvern instrument detects the scattered light intensity and converts this to a Fd and allows for the calculation of u. Particle velocities are usually expressed as electrophoretic mobilities. The electrophoretic mobility (EM) of a particle is defined as follows:

$$EM = u/\text{field strength}$$

The zeta potential (ZP) can be calculated by application of the Smoluchowski equation since the measurements are to be carried out at low ionic strengths and with relatively large particles, $$ZP = 4 \eta u/e$$

where $\eta$ is the viscosity of the medium, e is the dielectric constant and u is the particle velocity, respectively.

Electrophoretic mobility measurements are carried out by dispersing microspheres in 10 ml buffer solution such as phosphate or McIlvaine buffer from 100 $\mu$g–1 mg, with a constant ionic strength 0.1M. Four readings are taken using a PC4 wide capillary cell at a voltage of 100 volt, electrode spacing of 50 mm and a dielectric constant of 78.54.

The term 'solidified particles' is used herein to include made from a water soluble salt of chitosan that has been made insoluble in non-acid containing water by exposure to an alkaline agent. Exposure to the alkaline agent brings the chitosan out of solution so that it is no longer in its soluble salt form. Suitable alkaline agents for use include sodium hydroxide, calcium hydroxide, aluminium hydroxide, potassium hydroxide, sodium phosphate, sodium carbonate and ammonia. Particles, either powder or microspheres, treated in this way still retain a positive charge. For example, solidified chitosan microspheres can be prepared by emulsifying a chitosan or chitosan derivative salt into soya oil or a similar organic medium and adding an alkaline agent such as sodium hydroxide that solidifies (precipitates) the chitosan during mixing. The resultant solid microspheres will be positively charged in an aqueous suspension since no crosslinking has taken place.

If the particles are cross-linked, the degree of cross-linking must be such that the particles retain a positive charge in the range of +0.5 mV to +50 mV. If the particles are completely cross-linked and all available —NH$_2$ groups are used, they will become neutral or negatively charged. By partially cross-linking the chitosan, it is possible to leave the particles positively charged and partly soluble. The degree of cross-linking required is determined by measuring the zeta potential.

Partially crosslinked microspheres can be prepared using for example either emulsification or spray drying techniques. In the emulsification technique the chitosan solution is emulsified in an organic medium such as toluene or soya oil with an emulsifier such as SPAN 80™. A crosslinking agent in the form of for example glutaraldehyde or formaldehyde is either added to the organic phase before mixing with the chitosan solution or can be added after emulsification has taken place. The partly crosslinked microspheres can be harvested by filtration and washing.

The chitosan microspheres can be prepared by spray drying a solution of chitosan (0.05% w/v–0.5% at pH 3–7) containing an appropriate amount of glutaraldehyde or formaldehyde or similar crosslinking agent.

For obtaining positively charged chitosan microspheres the ratio of the crosslinking agent to chitosan should be 0.01 to 1.00 more preferably 0.05 to 0.75 and most preferably 0.1 to 0.6.

The zeta potential of the particles is preferably +1.0 mV to +45 mV and more preferably +1.5 mV to +40 mV, more preferably +2.0 mV to +35 mV more preferably +3.0 mV to +30 mV.

The chitosan or chitosan derivative or salt used preferably has a molecular weight of 4,000 or more, preferably in the range 25,000–2,000,000 and most preferably about 50,000–300,000. Chitosan or salts of chitosan may be used.

The term 'chitosan derivatives' is used herein to include ester, ether or other derivatives formed by interaction of acyl or allyl groups with the OH groups and not the NH$_2$ groups. Examples are O-alkyl ethers of chitosan, O-acyl esters of chitosan. Suitable derivatives are given in G.A.E. Roberts, Chitin Chemistry, MacMillan Press Ltd, London, 1992. Suitable salts of chitosan include nitrates, phosphates, sulphates, xanthates, hydrochlorides, glutamates, lactates, acetates.

The composition is preferably administered as a freeze dried formulation of the particles together with the active compound. The composition can also be prepared as a physical/mechanical mixture of the dried microspheres with the drug.

The microspheres may be prepared by spray drying, emulsification, solvent evaporation, precipitation or other methods known to a person skilled in the art. The active drug can be incorporated into the microspheres during their production or sorbed onto the microspheres after their production. The microspheres or powder can be partially cross-linked by glutaraldehyde, formaldehyde, benzydianone, benzoquinone, tripolyphosphate or other cross-linking agents known to the person skilled in the art. The conditions for carrying out the cross-linking, such as the amount of cross-linking agent required, are determined by monitoring the zeta potential and adjusting the conditions until the required zeta potential is obtained.

The size of the cross-linked or solidified microspheres are 1–200 $\mu$m, more preferably 1–100 $\mu$m.

If desired, other materials may be included in the composition, for example absorption enhancers. Suitable absorption enhancers include phospholipids such as lysophosphatidylcholine, lysophosphatidylglycerol and generally those mentioned in WO 88/09163.

The term "pharmacologically active compound" includes drugs, genes (DNA) or gene constructs, vaccines and components thereof (for example isolated antigens or parts thereof) and monoclonal antibodies.

The compositions may be used with drugs selected from the following non-exclusive list: insulin, PTH (parathyroid hormone), PTH analogues, calcitonins (for example porcine, human, salmon, chicken or eel) and synthetic modifications thereof, enkephalins, LHRH (lutenising hormone releasing hormone) and analogues (nafarelin, buserelin, leuprolide, goserelin), glucagon, TRH (Thyrotrophine releasing hormone), Vasopressin, Desmopressin, growth hormone, heparins, GHRH (growth hormone releasing hormone), nifedipine, THF (thymic humoral factor), CGRP (calcitonin gene related peptide), atrial natriuretic peptide, metoclopramide, ergotamine, Pizotizin, vaccines (particularly AIDS vaccines, measles, rhinovirus Type 13 and respiratory syncytial virus, influenza vaccines, pertussis vaccines, meningococcal vaccines, tetanus vaccines, diphtheria vaccines, cholera vaccines, DNA vaccines), pentamidine and CCK (cholecystokinin).

Further drugs include: antibiotics and antimicrobial agents such as tetracycline hydrochloride, leucomycin, penicillin, penicillin derivatives, erythromycin, sulphathiazole and nitrofurazone; antimigraine compounds such as sumatriptan or other 5-$HT_1$ agonists; vasoconstrictors such as phenylephrine hydrochloride, tetrahydrozoline hydrochloride, naphazoline nitrate, oxymetazoline hydrochloride and tramazoline hydrochloride: cardiotonics such as digitalis and digoxin; vasodilators such as nitroglycerine and papaverine hydrochloride; bone metabolism controlling agents such as vitamin D and active vitamin $D_3$; sex hormones; hypotensives; sedatives; anti-tumor agents; steroidal anti-inflammatory agents such as hydro-cortisone, prednisone, fluticasone, prednisolone, triamcinolone, triamcinolone acetonide, dexamethasone, betamethasone, beclomethasone and beclomethasone dipropionate; non-steroidal anti-inflammatory agents such as acetaminophen, aspirin, aminopyrine, phenylbutazone, mefanic acid, ibuprofen diclofenac sodium, indomethacin, colchicine and probenecid; enzymatic anti-inflammatory agents such as chymotrypsin and bromelain seratiopeptidase; antihistaminic agents such as diphenhydramine hydrochloride, chlorpheniramine maleate and clemastine; antitussive-expectorants such as codeine phosphate and isoproterenol hydrochloride; analgesics such as morphine and its polar metabolites such as morphine-6-glucuronides and morphine-3-sulphate; antiemetics such as metoclopramide, ondansetron, chlorpromazine; drugs for treatment of epilepsy such as Clonazepam; drugs for treatment of sleeping disorders such as melatonin; drugs for treatment of asthma such as salbutamol.

The compositions can be administered via the nasal route as a powder using a nasal powder device, via the vaginal route as a powder using a powder device, formulated into a vaginal suppository or pessary or vaginal tablet or vaginal gel and via the pulmonary route using a powder inhaler or metered dose inhaler, via the rectal route formulated into suppositories and via the small intestine or colonic route formulated in tablets or capsules. The compositions may gel on the mucosa at least to some extent and this may facilitate retention of the composition on the mucosa.

Further disclosed is a method of treating a human or other mammal by administering a composition as described above to a mucosal surface of that human or other mammal, for example the vagina, rectum, lungs, eye, colon or nasal cavity.

Preferred embodiments of the compositions and methods will be further understood from the following non-limiting examples.

EXAMPLE 1

Partially cross-linked Microspheres Were Prepared as Follows 1 g of Span 80 was mixed into 200 ml of soya oil. The oil/Span mixture was divided into two; one half was heated to 120° C. Into the remaining 100 ml of oil/Span was emulsified (Silverson homogeniser, 7000 rpm/3 min) 5 ml of a 10% w/v aqueous solution of low viscosity chitosan hydrochloride (Sea Cure CL113, Pronova, Drammen, Norway). The emulsion was poured into the hot oil/Span mixture and stirred at 1500 rpm using an overhead stirrer. After 10 minutes, the oil/Span/chitosan mixture was transferred to an ice bath and allowed to cool <40° C. while stirring continued. 100 ml of acetone was added and the mixture centrifuged (2500 rpm/5 min). The microspheres were washed with acetone, collected by filtration and allowed to dry. The entire process was repeated until 800 mg of microspheres had been prepared. The microspheres were stirred into a mixture of 40 ml of acetone and 10 ml of 38% w/v formaldehyde solution. After 24 hours the microspheres were recovered by filtration and resuspended in 100 ml of acetone. After a further 24 hours, the microspheres were recovered by filtration and dried at room temperature. The size of the microspheres was in the range 1–50 µm.

EXAMPLE 2

Partially Cross-linked Microspheres Were Prepared as Follows

To 200 ml of soya oil was added 1 g of Span 80. The oil was stirred using an overhead mixer at 1000 rpm and 0.5 ml of 25% aqueous glutaraldehyde was added. After stirring for 30 minutes, 10 ml of a 5% w/v aqueous solution of low viscosity chitosan hydrochloride (Sea Cure CL113, Pronova, Drammen, Norway) was added to the oil/glutaraldehyde emulsion. After stirring at 1000 rpm for a further 75 minutes, 200 ml of acetone was added to the emulsion. The mixture was then centrifuged (2500 rpm/5 min). The microsphere pellets were resuspended in acetone, recovered by filtration, rinsed with further acetone and dried at room temperature. The majority of the microspheres were in the size range 10–50 µm.

EXAMPLE 3

Partially Cross-linked Powder was Prepared as Follows

Into a beaker was weighed 1 g of chitosan hydrochloride (Sea Cure CL113) powder. To the chitosan powder was added 80 ml of acetone and 20 ml of formaldehyde solution (38% w/v in water/methanol). The beaker contents were stirred for 24 hours. The cross-linked chitosan powder was recovered by filtration, and suspended in 200 ml of acetone. After 24 hours, the chitosan was recovered by filtration and dried in an oven at 50° C. for 48 hours. The mean particle size of the cross-linked powder was 20 µm.

EXAMPLE 4

Solidified Chitosan Microspheres Were Prepared as Follows

A 2% w/v aqueous solution of medium viscosity chitosan glutamate (Sea Cure +210) was prepared. 10 ml of chitosan solution was emulsified (8000 rpm/10 min) into 100 ml of soya oil. 100 ml of 10% w/v sodium hydroxide solution was added and stirring continued at 8000 rpm for 5 min. The mixture was then mixed with a magnetic stirrer bar for a further 30 min. The microspheres were collected by centrifugation and washed with petroleum ether, then ethanol, and finally hot distilled water. Microspheres of mean diameter 25 µm were obtained with a surface charge of +3.7 mV.

EXAMPLE 5

Partially Cross-linked Microspheres Were Prepared as Follows

A 3% w/v aqueous solution of medium viscosity chitosan glutamate (Sea Cure +210) was prepared. 10 ml of chitosan solution was emulsified (8000 rpm/2 min) into a mixture of 100 ml of toluene and 1 g of Span 85.

2 ml of 8% w/v glutaraldehyde solution was added and the emulsion left to gently mix, using a magnetic stirrer bar, for 12 hours. The microspheres were collected by filtration, washed with toluene, and then ethanol, and left to dry.

EXAMPLE 6

Partially Cross-linked Microspheres Were Prepared as Follows 250 ml of a solution of 0.2% w/v chitosan in 1% acetic acid was prepared. 2 ml of 4% glutaraldehyde solution was added and the solution was spray-dried (Lab-Plant SD 04 spray-drier) using a drying temperature of 160° C. and a flow rate of 5–10 ml/min. Chitosan microspheres of 5 $\mu$m diameter and a zeta potential of +5.7 mV were obtained.

EXAMPLE 7

600 mg of microspheres prepared using the method described in Example 1 were weighed into a 100 ml volumetric flask. To the microspheres were added 30 ml of water and 10 ml of sodium insulin solution (60 IU/ml). The flask contents were swirled intermittently for 20 minutes and then frozen by immersing the flask into liquid nitrogen. The frozen contents were transferred to a freeze-drier and lyophilised. The lyophilised formulation was administered nasally to each of four sheep at an insulin dose of 2 IU/kg (equivalent to 2 mg/kg of chitosan microspheres). As a control, a solution of 200 IU/ml insulin in 5 mg/ml medium viscosity chitosan solution was administered intranasally at 2 IU/kg. Blood samples were taken and plasma glucose concentrations measured. The mean changes in plasma glucose concentration with time for the two formulations is shown in FIG. 1. It can be seen that the fall in plasma glucose was of greater magnitude and more prolonged with the microsphere formulation of the invention than with the chitosan solution.

EXAMPLE 8

Figure 2:
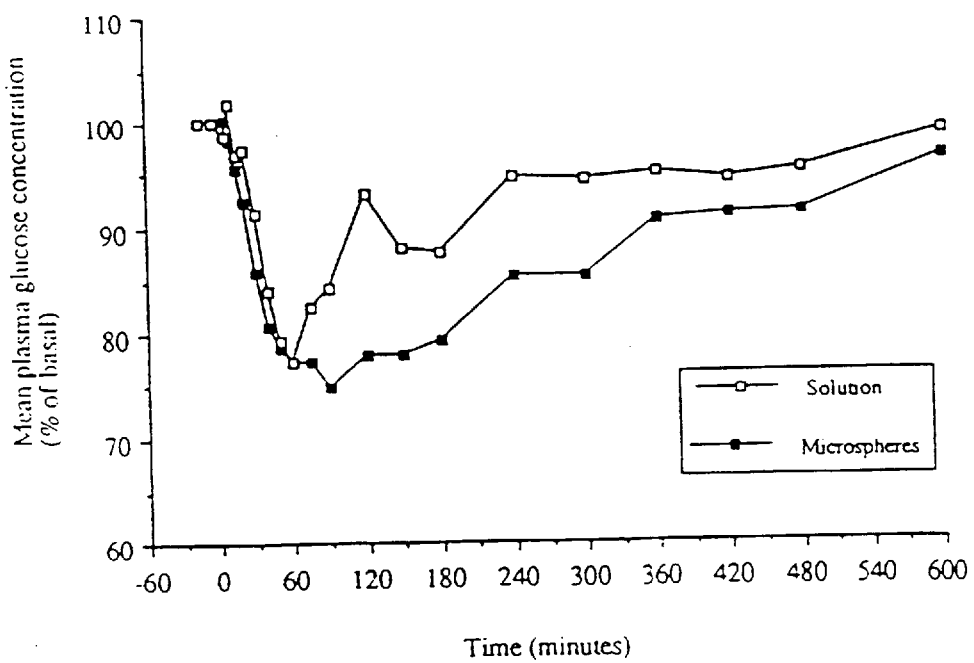
FIG. 2 is a graph showing the mean plasma glucose/time curves after administration to sheep of 2 IU/kg insulin in chitosan solution and with chitosan microspheres (prepared by adding glutaraldehyde to chitosan emulsion).

A lyophilised formulation containing insulin was prepared from 600 mg of the microspheres described in Example 2 using the method described in Example 7. The lyophilised formulation was administered nasally to each of four sheep at an insulin dose of 2 IU/kg (equivalent to 2 mg/kg of chitosan microspheres). The chitosan solution formulation described in Example 7 was also administered. Blood samples were taken and plasma glucose concentrations measured. The mean changes in plasma glucose with time for the two formulations are shown in FIG. 2. Although the minimum glucose concentration achieved was similar for both formulations, the duration of action achieved with the microsphere formulation was significantly prolonged compared with the chitosan solution.

EXAMPLE 9

Figure 3:
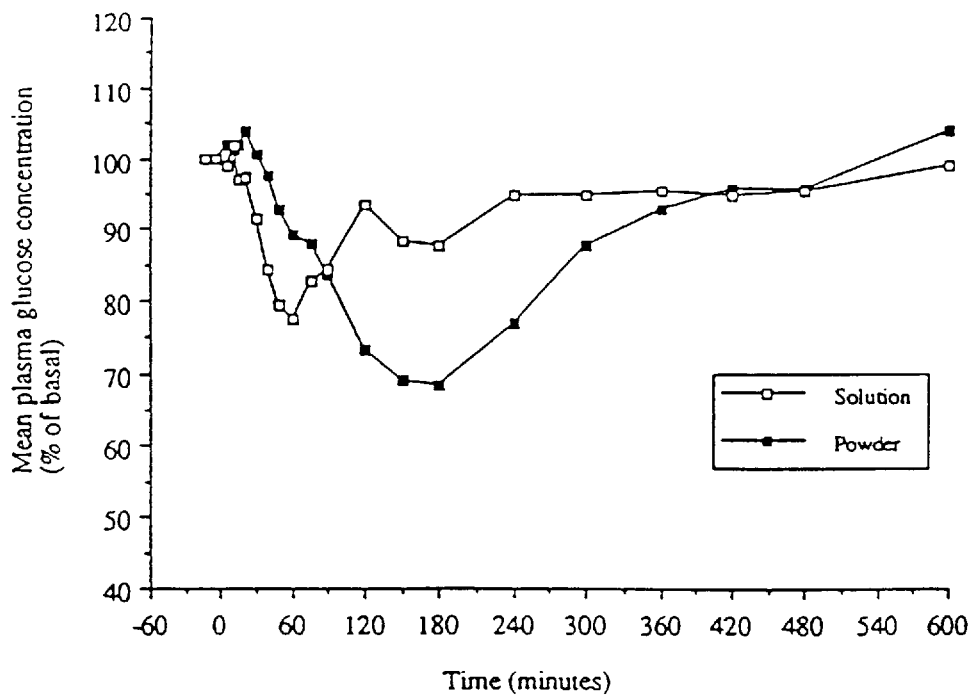
FIG. 3 is a graph showing the mean plasma glucose/time curves after administration to sheep of 2 IU/kg insulin in chitosan solution and with cross-linked chitosan powder.

A lyophilised formulation containing insulin was prepared from 600 mg of the cross-linked powder described in Example 3 using the method described in Example 7. The lyophilised formulation was administered nasally to each of four sheep at an insulin dose of 2 IU/kg (equivalent to 2 mg/kg of chitosan powder). The chitosan solution formulation described in Example 7 was also administered. Blood samples were taken and plasma glucose concentrations measured. The mean changes in plasma glucose with time for the two formulations are shown in FIG. 3. The fall in plasma glucose was of greater magnitude and more prolonged with the microsphere formulation of the invention compared with the chitosan solution.

EXAMPLE 10

Figure 4:
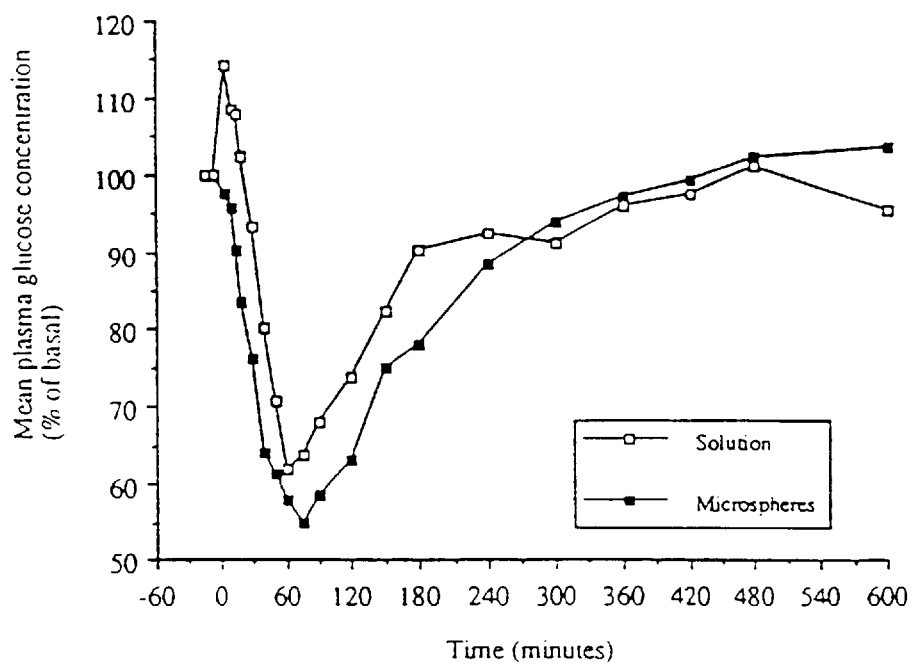
FIG. 4 is a graph showing the mean plasma glucose/time curves after administration to sheep of 2 IU/kg insulin in chitosan solution and with chitosan microspheres (prepared by precipitation with sodium hydroxide).

A lyophilised formulation containing insulin was prepared from 600 mg of the microspheres described in Example 4 using the method described in Example 7. The lyophilised formulation was administered nasally to each of four sheep at an insulin dose of 2 IU/kg (equivalent to 2 mg/kg of chitosan microspheres). The chitosan solution formulation described in Example 7 was also administered. Blood samples were taken and plasma glucose concentrations measured. The mean changes in plasma glucose with time for the two formulations are shown in FIG. 4.

EXAMPLE 11

Figure 5:
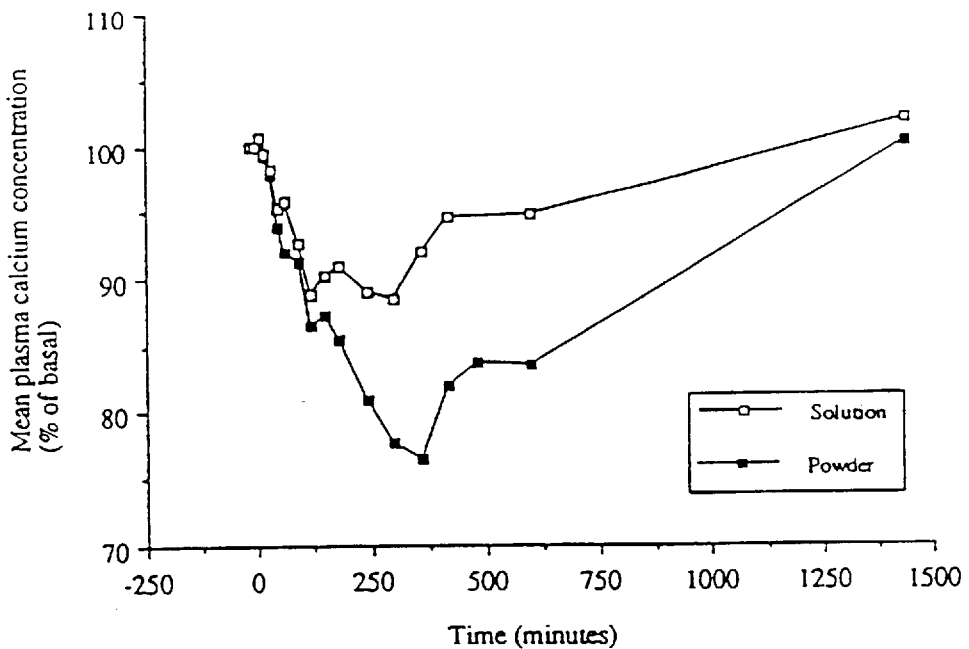
FIG. 5 is a graph showing the mean plasma calcium concentrations after nasal administration to sheep of 20 IU/kg salmon calcitonin in chitosan solution and with cross-linked chitosan powder.

Into a 100 ml conical flask was weighed 880 mg of the cross-linked powder described in Example 3. To the powder was added 53.7 ml of water and 5 ml of salmon calcitonin solution (1760 IU/ml) The flask contents were swirled intermittently for 20 minutes and then frozen by immersing the flask into liquid nitrogen. The frozen contents were transferred to a freeze-drier and lyophilised. The lyophilised formulation was administered nasally to four sheep at a salmon calcitonin dose of 20 IU/kg (equivalent to 2 mg/kg of chitosan powder). As a control, a solution of 2000 IU/ml salmon calcitonin in 5 mg/ml medium viscosity chitosan solution was administered intranasally at 20 IU/kg. Blood samples were taken and plasma calcium concentrations measured. The changes in plasma calcium concentration with time for the two formulations are shown in FIG. 5. For the chitosan powder formulation, the fall in plasma calcium, indicative of calcitonin absorption, was markedly greater and more prolonged than for the chitosan liquid formulation.

EXAMPLE 12

Figure 6:
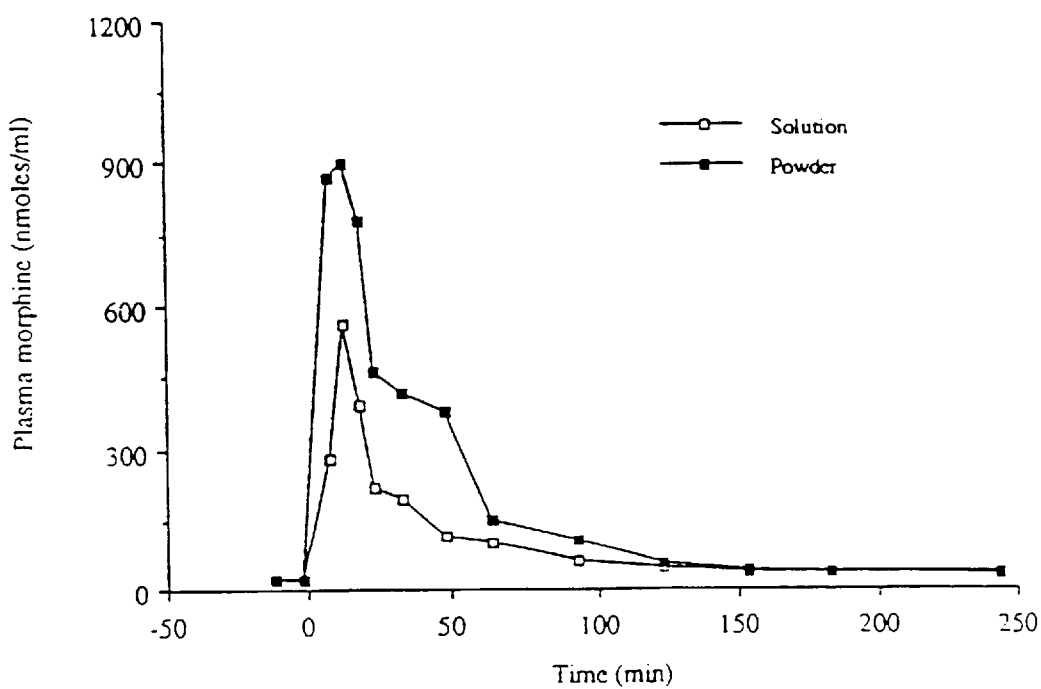
FIG. 6 is a graph showing the plasma morphine concentrations following nasal administration of morphine HCl in chitosan solution or with cross-linked chitosan.

Into a 250 ml conical flask was weighed 800 mg of the cross-linked powder described in Example 3. To the powder was added 48.3 ml of water and 5 ml of 24 mg/ml morphine hydrochloride solution. The flask contents were swirled intermittently for 20 minutes and then frozen by immersing the flask into liquid nitrogen. A solution was prepared containing 30 mg/ml morphine hydrochloride in medium viscosity chitosan glutamate solution, adjusted to pH 4. The cross-linked chitosan powder and the chitosan liquid formulation were each dosed intranasally to a group of four sheep at a morphine hydrochloride dose of 0.3 mg/kg. Plasma samples were collected and analysed for morphine content using a radioimmunoassay. The concentration time curves for the two formulations are shown in FIG. 6. The peak plasma concentration achieved was approximately 50% higher for the chitosan powder formulation than for the chitosan liquid formulation.

EXAMPLE 13

Into a 500 ml conical flask was weighed 1400 mg of the cross-linked powder described in Example 3. To the powder was added 90 ml of water and 3.1 ml of salmon calcitonin solution (9000 IU/ml). The flask contents were swirled intermittently for 20 minutes and then frozen by immersing the flask into liquid nitrogen. The frozen contents were transferred to a freeze-drier and lyophilised. 18.54 g of Suppocire BS2X (Gattefosse) was weighed into a beaker and melted at 35° C. 0.36 g of the freeze-dried calcitonin/chitosan mixture was mixed into the melted Suppocire. The mixture was poured into each of four 5 g pessary moulds.

Figure 7:
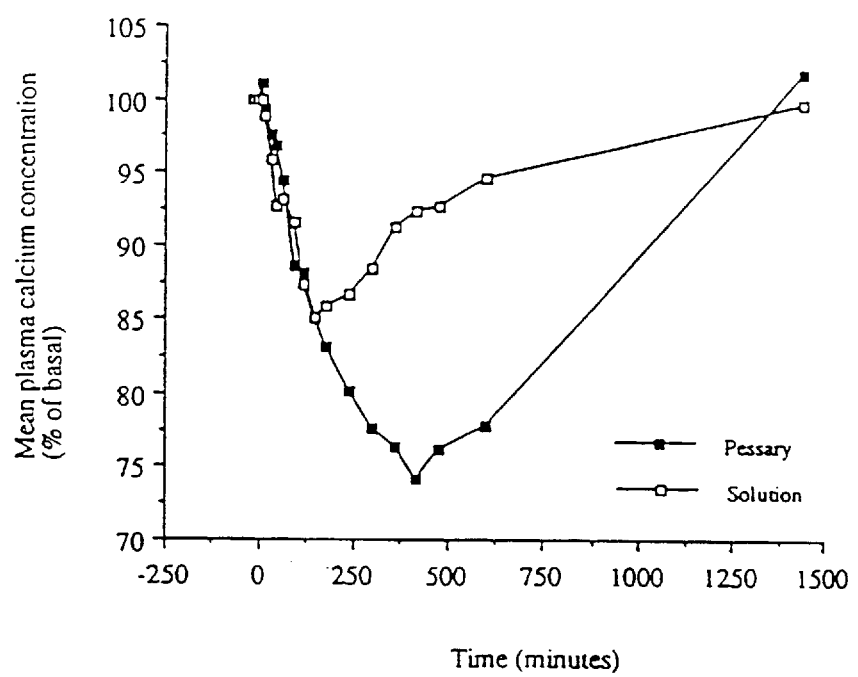
FIG. 7 is a graph showing the plasma calcium concentrations in sheep following the vaginal administration of salmon calcitonin (1600 IU) in a pessary containing cross-linked chitosan or as a solution.

The pessaries were allowed to set, removed from the mould, and trimmed to a weight of 4.2 g. The pessaries were administered intravaginally to each of four sheep. An aqueous solution containing 1600 IU/ml of salmon calcitonin was also administered intravaginally to four sheep. The changes in plasma calcium concentration with time for the pessary formulation and aqueous solution are shown in FIG. 7. The fall in plasma calcium, indicative of calcitonin absorption, was markedly greater in magnitude and duration for the pessary formulation than for the solution.

EXAMPLE 14

Figure 8:
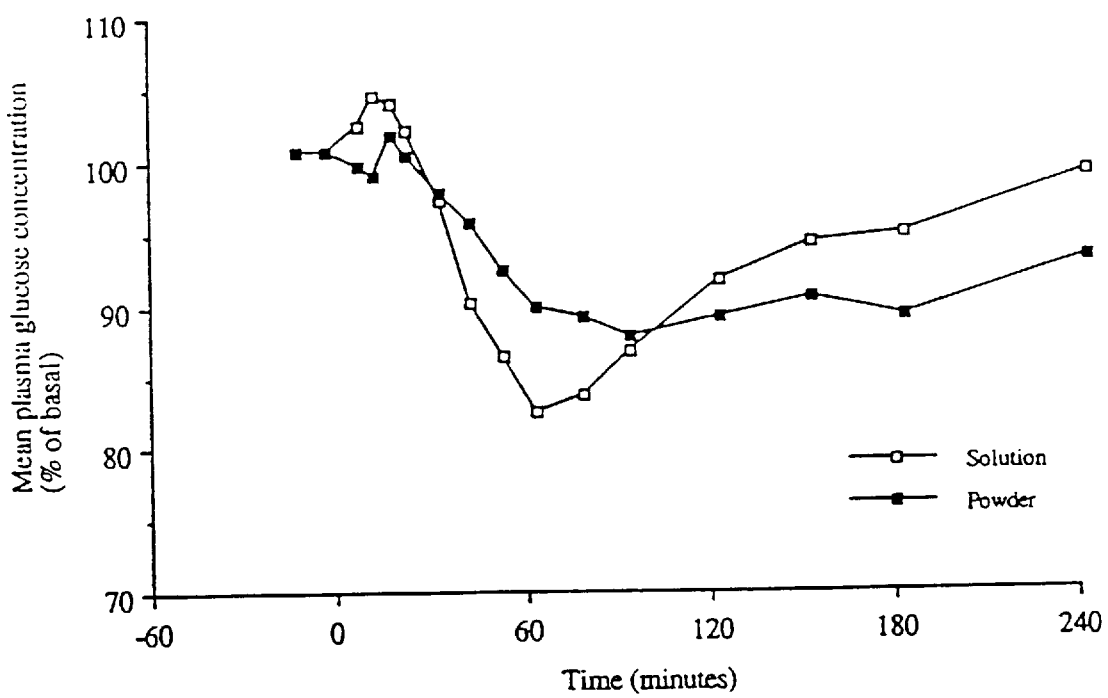
FIG. 8 is a graph showing the mean plasma glucose/time curves after administration to sheep of 2 IU/kg insulin in chitosan solution and as a freeze-dried chitosan/lactose powder.

The effect of a chitosan solution formulation on the nasal absorption of insulin in sheep was compared with the effect of a chitosan powder formulation in which the chitosan had not been treated in any way. A solution of 200 IU/ml insulin in 5 mg/ml medium viscosity chitosan solution was administered intranasally at 2 IU/kg to sheep. The powder formulation was prepared by mixing 640 IU insulin with 80 mg chitosan HCl 211 and 720 mg lactose and administered to the sheep at 2 IU/kg. Blood samples were taken and plasma glucose concentrations measured. The mean changes in plasma glucose concentration with time for the two formulations is shown in FIG. 8. The fall in plasma glucose was less pronounced for the powder formulation than for the chitosan solution.

EXAMPLE 15

Figure 9:
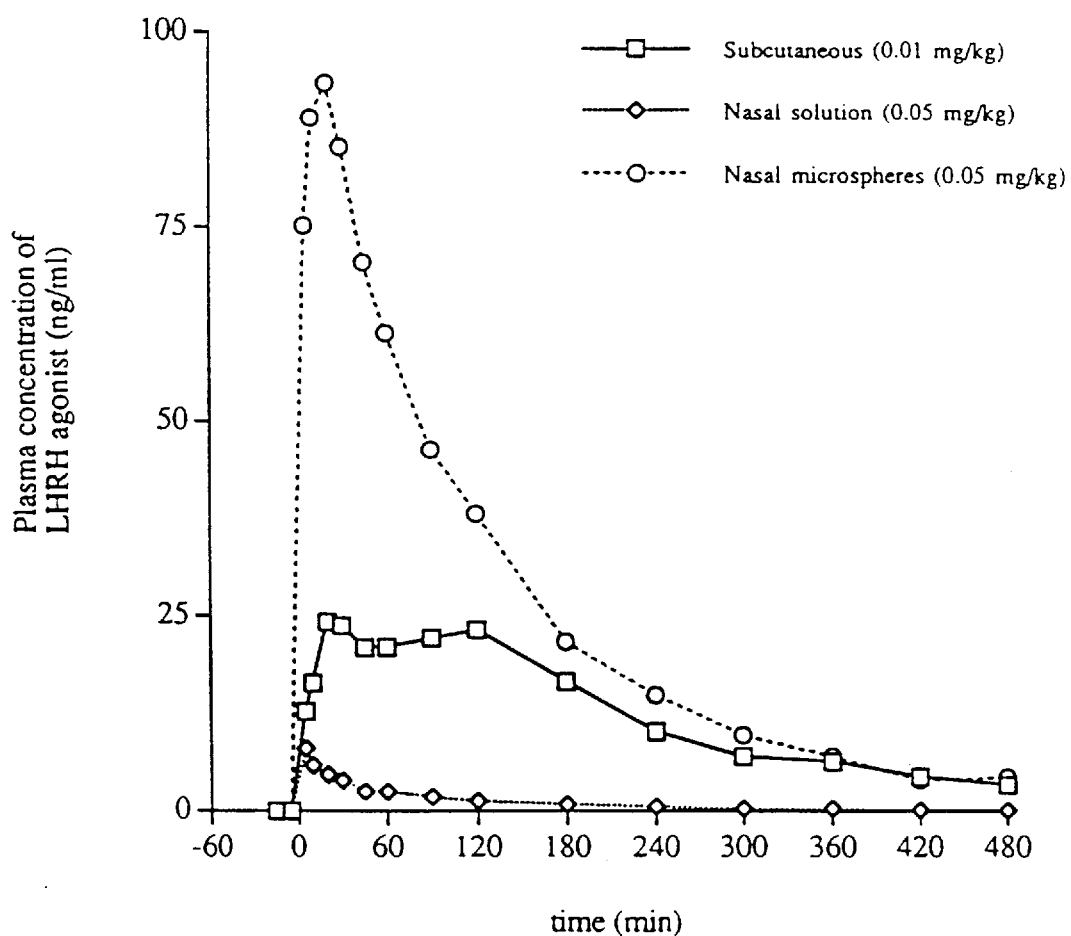
FIG. 9 is a graph showing the plasma concentration of LHRH agonist in sheep after intranasal and subcutaneous administration.

Into a 100 ml conical flask were weighed 640 mg of the microspheres described in Example 2. To the microspheres were added 26.7 ml of water and 16 ml of a solution containing 1 mg/ml of a LHRH agonist. The suspension was frozen and lyophilised. The lyophilised formulation was administered nasally to each of four sheep at a dose of 2.05 mg/kg (=0.05 mg/kg of LHRH agonist). As controls, four sheep received, nasally, 0.05 mg/kg of LHRH agonist as an aqueous solution and four sheep received 0.01 mg/kg as a subcutaneous injection. Plasma samples were collected and the LHRH agonist content was measured using a radioimmunoassay. In FIG. 9, the concentration vs. time profiles are shown for the microsphere formulation, the nasal solution and the subcutaneous injection. The microsphere formulation resulted in a marked enhancement in nasal absorption of the LHRH agonist. Compared to the subcutaneous injection, the mean bioavailabilities of the microsphere formulation and control solution were 1.5% and 36.6% respectively.

EXAMPLE 16

Into a 100 ml conical flask was weighed 640 mg of the microspheres described in Example 2. To the powder was added 26.7 ml of water and 16 ml of a solution containing 1 mg/ml of a LHRH agonist. 28 g of Suppocire BS2X (Gattefosse) was weighed into a beaker and melted at 35° C. 0.56 g of the freeze-dried LHRH/microsphere mixture was mixed into the melted Suppocire. The mixture was poured into each of five 5 g pessary moulds. The pessaries were allowed to set, removed from the mould, and trimmed to a weight of 4.2 g (=2 mg of LHRH agonist/pessary). The pessaries were administered intravaginally to each of four sheep.

A gel formulation was prepared by suspending 0.6 g of the microspheres described in Example 2 in 10 ml of a solution containing 1.5 mg/ml LHRH agonist. 1.42 g of the gel formulation (=2 mg of LHRH agonist) was administered to each of four sheep from two syringes (two 1 ml syringes, each containing 0.71 g of gel).

Four sheep were administered, intravaginally, 0.4 ml of a 5 mg/ml solution of LHRH agonist.

Figure 10:
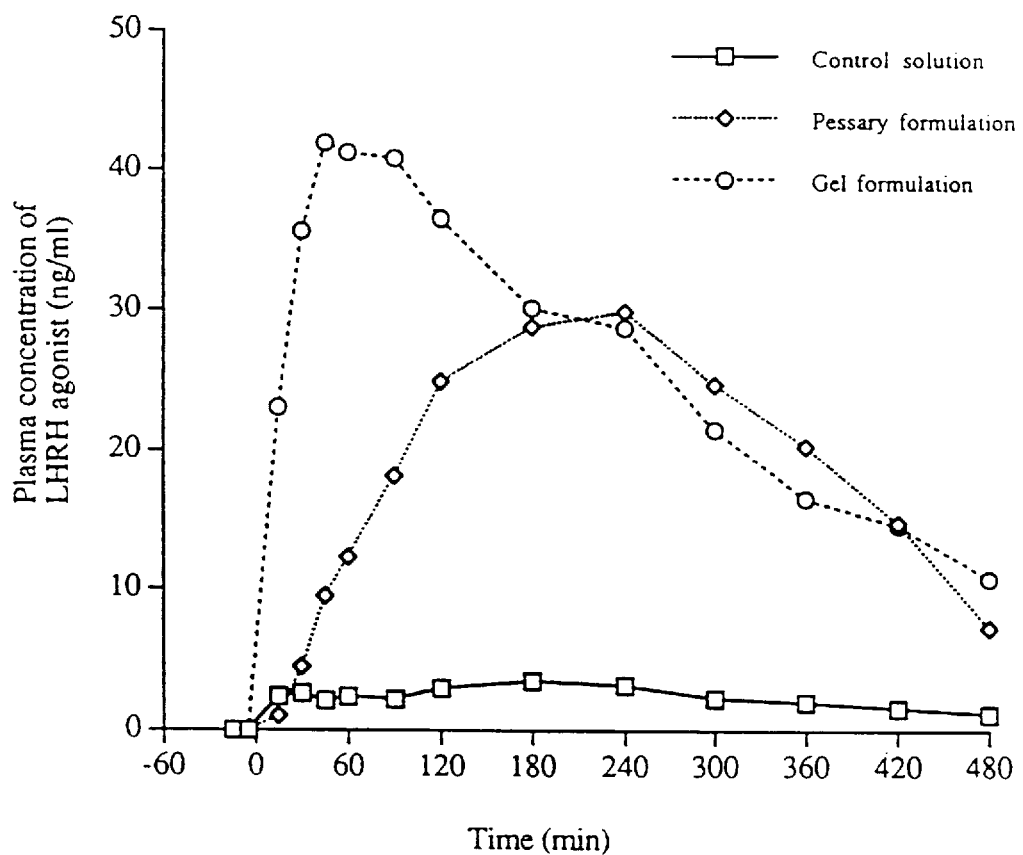
FIG. 10 is a graph showing the plasma concentration of LHRH agonist in sheep after vaginal administration of formulations containing chitosan microspheres.
Figure 11:
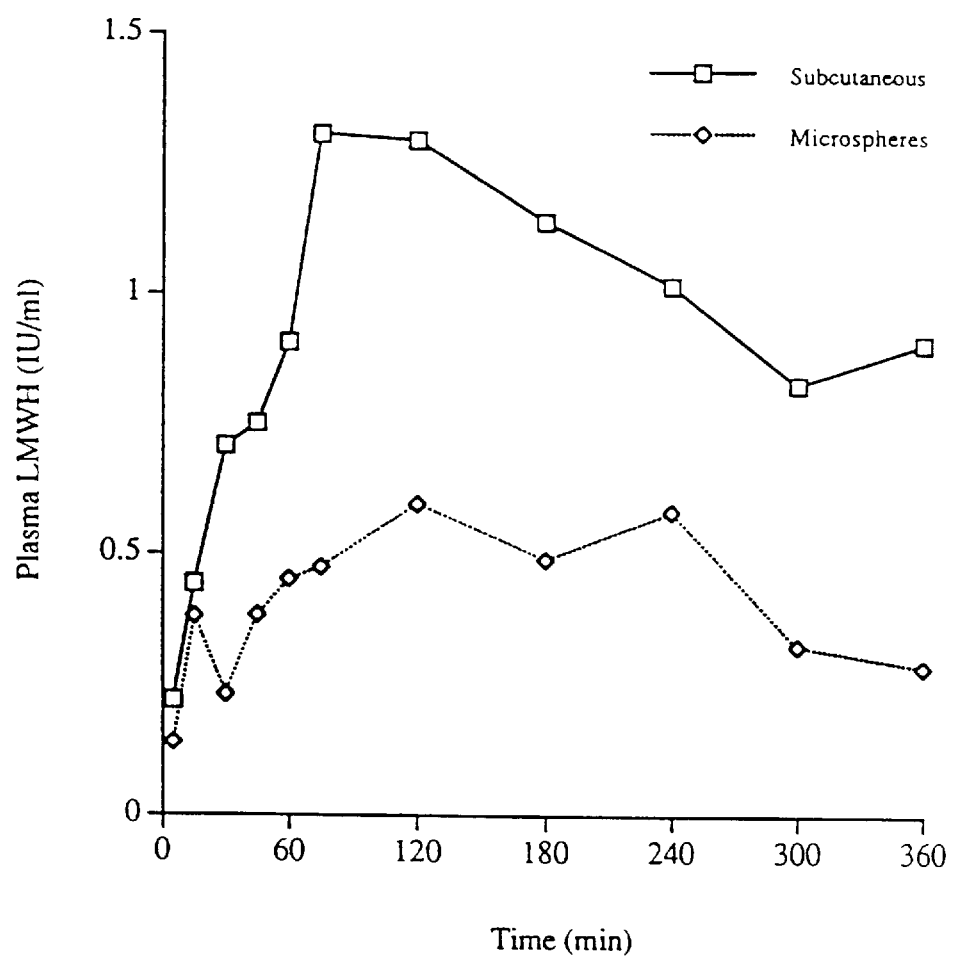
FIG. 11 is a graph showing the plasma concentrations of LMWH following administration of subcutaneous solution and nasal microsphere formulations.

Plasma samples were collected and assayed for LHRH agonist content. Plasma concentration vs. time profiles for the control solution and two vaginal formulations are shown in FIG. 10.

The two formulations containing chitosan microspheres substantially enhanced the vaginal absorption of LHRH agonist. Compared to the subcutaneous control (Example 15), the bioavailabilities of the control solution, gel formulation and pessary formulation were 4.7%, 46.0% and 32.9% respectively.

EXAMPLE 17

Into a 100 ml flask was weighed 640 mg of the microspheres described in Example 2. To the flask was added 27 ml of water and 16 ml of a 50 mg/ml aqueous solution of low molecular weight heparin (LMWH). The suspension was frozen and lyophilised. The lyophilised formulation was administered intranasally to four sheep at 4.5 mg/kg (=2.5 mg/kg LMWH). As a control, four sheep received 1.25 mg/kg LMWH as a subcutaneous injection. Plasma samples were collected and the anti-factor Xa activity measured using a proprietary assay kit. By measuring the anti-factor Xa activity in standards containing known quantities of LMWH, the LMWH content of the sheep plasma samples was calculated. The plasma LMWH concentration vs. time profiles for the nasal and subcutaneous formulations are shown in FIG. 1. Relative to the subcutaneous dose. The mean bioavailability of the nasal chitosan formulation was 19%.

EXAMPLE 18

Figure 12:
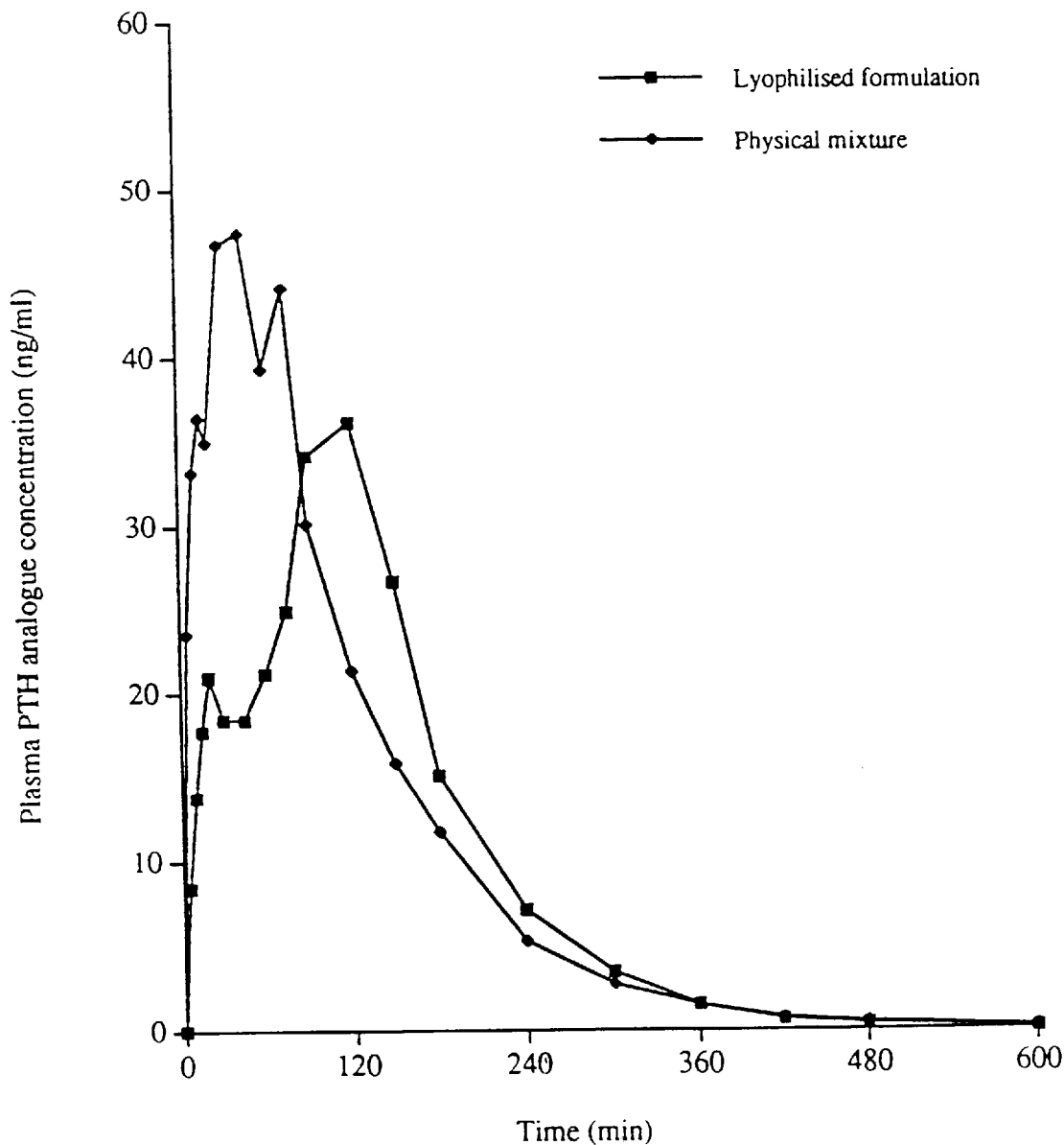
FIG. 12 is a graph showing the plasma concentration of PTH analogue following nasal administration of two chitosan powder formulations to sheep.

Into a 100 ml flask was weighed 560 mg of the cross-linked chitosan powder described in Example 3. To the flask was added 37 ml of an aqueous solution containing 28 mg of a parathyroid hormone (PTH) analogue. The suspension was frozen and lyophilised. A physical mixture of cross-linked chitosan powder and PTH analogue was prepared by blending together 560 mg of cross-linked chitosan powder (Example 3) and 28 mg of PTH analogue. Blending was performed using a pestle and mortar. The two powder formulations were administered intranasally to four sheep at 2.1 mg/kg (=0.1 mg/kg PTH analogue). As a control, four sheep received 0.01 mg/kg PTH analogue as an intravenous injection. Plasma samples were collected and the PTH analogue content measured using a radioimmunoassay technique. The plasma PTH analogue concentration vs. time profiles for the intravenous and two nasal and doses are shown in FIG. 12. Relative to the intravenous dose, the mean bioavailabilities of the lyophilised and physical mixture formulations were 20.7% and 18.0% respectively.

We claim:

1. A drug delivery composition for administration to mucosa comprising a pharmacologically active compound and particles of chitosan or a chitosan derivative or salt, wherein the particles are either solidified or partially crosslinked such that they have a zeta potential of +0.5 to +50 mV, measured by microelectrophoresis for microspheres having a diameter of 5 µm or more and by laser Doppler anemometry for microspheres having a diameter of less than 5 µm at pH 7.4 and 0.1M ionic strength.

2. A composition according to claim 1 wherein the size of the chitosan particles is between one and 100 µm.

3. A composition according to claim 1 wherein the particles are in a form selected from the group consisting of powder and microspheres.

4. A composition according to claim 1 wherein the pharmacologically active compound is a peptide.

5. A composition according to claim 4 wherein the pharmacologically active compound is insulin.

6. A composition according to claim 4 wherein the pharmacologically active compound is calcitonin.

7. A composition according to claim 4 wherein the pharmacologically active compound is PTH.

8. A composition according to claim 1 wherein the pharmacologically active compound is an antimigraine compound.

9. A composition according to claim 1 wherein the pharmacologically active compound is morphine.

10. A composition according to claim 1 wherein the pharmacologically active compound is a polar molecule.

11. A composition according to claim 1 further comprising an absorption enhancing material.

12. A composition according to claim 1 wherein the composition is in a form suitable for administration to the mucosa of the nasal cavity, vagina, rectum, lungs, buccal cavity, eye, small intestine or colon.

13. A method of delivering a pharmacologically active compound across a mucosal surface comprising administering a composition to the mucosal surface, wherein the composition comprises a pharmacologically active compound and particles of chitosan or a chitosan derivative or salt, wherein the particles are either solidified or partially cross-linked such that they have a zeta potential of +0.5 to +50 mV, measured by microelectrophoresis for microspheres having a diameter of 5 µm or more and by laser Doppler anemometry for microspheres having a diameter of less than 5 µm at pH 7.4 and 0.1M ionic strength.

* * * * *